United States Patent [19]
Okamoto

[11] Patent Number: 5,971,932
[45] Date of Patent: Oct. 26, 1999

[54] OSCILLOMETRIC TYPE ELECTRONIC SPHYGMOMANOMETER

[75] Inventor: Makoto Okamoto, Tokyo, Japan

[73] Assignee: Citizen Watch Co., Ltd., Tokyo, Japan

[21] Appl. No.: 09/114,273

[22] Filed: Jul. 13, 1998

[30] Foreign Application Priority Data

Jul. 18, 1997 [JP] Japan ..................................... 9-193691

[51] Int. Cl.⁶ ..................................................... A61B 5/00
[52] U.S. Cl. ......................... 600/493; 600/493; 600/494; 600/495
[58] Field of Search ........................... 600/490, 493–496, 600/506

[56] References Cited

U.S. PATENT DOCUMENTS

| | | |
|---|---|---|
| 4,703,760 | 11/1987 | Miyawaki et al. . |
| 4,922,918 | 5/1990 | Ruiter . |
| 5,385,149 | 1/1995 | Chang et al. ............................ 600/494 |
| 5,542,428 | 8/1996 | Jayne ...................................... 600/494 |
| 5,551,440 | 9/1996 | Miyawaki ............................... 600/494 |
| 5,759,157 | 6/1998 | Harada et al. .......................... 600/495 |

Primary Examiner—Robert L. Nasser
Attorney, Agent, or Firm—Kaensaka & Takeuchi

[57] ABSTRACT

An oscillometric type electronic sphygmomanometer for determining the systolic and the diastolic blood pressure on the basis of a peak formed by the variance in the pulse wave amplitude, wherein the systolic and the diastolic blood pressure are provisionally determined on the basis of the curve of the varying pulse wave amplitude which forms the first peak, when the provisionally determined diastolic blood pressure is higher than a preset value, the pulse wave amplitude continues to be detected and monitored until the cuff pressure decreases below the provisionally determined diastolic blood pressure by a predetermined pressure, and when the pulse wave amplitude detected while being monitored is equal to or higher than the said maximum pulse wave amplitude value, the pulse wave amplitude continues to be further detected so as for a new maximum pulse wave amplitude to be obtained, thereby determining at least the diastolic blood pressure on the basis of the curve of the varying pulse wave amplitude, which has the maximum pulse wave amplitude value and forms the second peak. As a result of such a configuration, it will become possible to avoid an erroneous measurement of the blood pressure caused by disordered breathing and physical movement of the testee when his/her the blood pressure is measured.

13 Claims, 5 Drawing Sheets

OSCILLOMETRIC TYPE ELECTRONIC SPHYGMOMANOMETER

BACKGROUND OF THE INVENTION

1. Field of the Invention

The present invention relates to an oscillometric type electronic sphygmomanometer which determines (measures) the blood pressure by the steps of compressing an artery with an inflated cuff, detecting pulse wave amplitude while the inflated cuff being deflated and comparing the pressure provided by the cuff on the artery with the pulse wave amplitude.

2. Description of Related Art

When an oscillometric type electronic sphygmomanometer is used, the blood pressure can be measured by the steps of wrapping a cuff around the brachium of a testee or examinee, who may be a patient, for example, compressing the brachium and the like so as for an artery to be occluded by raising the pressure in the cuff, detecting the pressure in the cuff by the means of detecting cuff pressure as the inflated cuff being deflated, detecting pulse wave components superimposed on the signal indicative of the pressure in the cuff (cuff pressure) by the means of detecting pulse wave amplitude, converting the pulse wave information of the pulse wave components into a series of pulse wave amplitudes by the means of detecting pulse wave amplitude, and determining the blood pressure of the testee on the basis of the maximum value of the series of pulse wave amplitudes and the cuff pressure. For example, the cuff pressure corresponding to the maximum pulse wave amplitude is determined as the mean the blood pressure, the cuff pressure corresponding to the pulse wave amplitude of the high pressure side which is equivalent to 50% of the maximum pulse wave amplitude as the systolic blood pressure, the cuff pressure corresponding to the pulse wave amplitude of the low pressure side which is equivalent to 70% of the maximum pulse wave amplitude as the diastolic blood pressure.

During the above process, the pulse wave amplitude gradually increases and then decreases as the cuff pressure changes, thereby forming a peak (a mountain-shaped curve). Normally the pulse wave amplitude changes by first increasing and then decreasing so that only one convex or peak is formed from the beginning to the end of decrease in the cuff pressure, which is as shown in FIG. 4. It is clinically known, however, that the change of the pulse wave amplitude may result in two peaks being formed as shown in FIG. 5 because of the disordered breathing of the testee or the physical movement of his/her body in measuring the blood pressure, or in the case of patients with high blood pressure.

In such cases, a conventional sphygmomanometer may determine the mean, the systolic and the diastolic blood pressure on the basis of the waveform of the pulse wave amplitude which forms the first peak the smaller of the two peaks, thereby generating a measurement containing an error.

An electronic sphygmomanometer has been proposed in Japanese Patent Publication (Kokoku) Hei6-28638 in order to overcome such a problem.

Although the curve passes through a possible maximum value of the pulse wave amplitude and begins to decrease, if the decrement from the possible maximum value is small, the electronic sphygmomanometer described in the Japanese Patent Publication above will not yet determine the true maximum value.

More particularly, it is determined whether $A(n) \leq \gamma \times Amax$ holds and if this inequality does not hold, then the possible maximum value will not be regarded as being the true maximum value by the sphygmomanometer and the measurement will be continued. In the above inequality, $A(n)$ is the measured pulse wave amplitude, Amax is the possible maximum value so far reached, and $\gamma$ is a predetermined multiplier which is multiplied to Amax and is in the range of 0.7–0.9, for example.

This sphygmomanometer of Japanese Patent Publication (Kokoku) Hei6-28638, however, suffers from the problem below. When the changes in the pulse wave amplitude result in forming two peaks in the entire curve and the decrement of the pulse wave amplitude which forms the first peak is large (for example, when $A(n)>0.7–0.9\times Amax$), the maximum value (therefore, the systolic blood pressure and the diastolic blood pressure) will be determined on the basis of the first peak, thereby generating an erroneous the blood pressure value.

OBJECT AND SUMMARY OF THE INVENTION

The object of the present invention is to provide a reliable oscillometric type electronic sphygmomanometer employing a measurement method wherein the pulse wave amplitude will be continuously monitored until the cuff pressure decreases below the diastolic blood pressure by a predetermined pressure value when the lowest pressure is higher than a certain value (preset value), thereby further determining whether the monitored amplitude will provide the new diastolic blood pressure and thus avoiding an erroneous measurement.

In accordance with the present invention, there is provided an oscillometric type electronic sphygmomanometer configured to determine the systolic and the diastolic blood pressure on the basis of a peak formed by the variance in the pulse wave amplitude, wherein at least the diastolic blood pressure is determined on the basis of the cuff pressure and pulse wave amplitude forming the peak which has the maximum pulse wave amplitude value when more than two peaks are formed on the curve.

In such an oscillometric type electronic sphygmomanometer, it is preferred that the systolic and the diastolic blood pressure are provisionally determined on the basis of the curve of the varying pulse wave amplitude which forms the first peak, when the provisionally determined diastolic blood pressure is higher than a preset value, the pulse wave amplitude continues to be detected and monitored until the cuff pressure decreases to the provisionally determined diastolic blood pressure by a predetermined pressure, and when the pulse wave amplitude detected while being monitored is equal to or higher than the said maximum pulse wave amplitude value, the pulse wave amplitude continues to be further detected so as for a new maximum pulse wave amplitude to be obtained, thereby determining at least the diastolic blood pressure on the basis of the curve of the varying pulse wave amplitude, which has the maximum pulse wave amplitude value and forms the second peak.

In such an oscillometric type electronic sphygmomanometer, an erroneous measurement of the blood pressure can be avoided since at least the diastolic blood pressure is not determined by the first peak on the curve of the varying pulse wave amplitude.

Also according to the present invention, if the pulse wave amplitude and the cuff pressure are detected and stored in a memory and then a the blood pressure is determined on the basis of the relationship between the pulse wave amplitude and the cuff pressure, the data representative of the pulse wave amplitude and the cuff pressure are stored in the memory only when the pulse wave amplitude detected while being monitored is higher than the predetermined ratio of the maximum pulse wave amplitude on the curve of the varying pulse wave amplitude which forms the first peak, and when the systolic and the diastolic blood pressure are determined on the basis of the curve of the varying pulse wave amplitude which forms the second peak, the data representative of the cuff pressure and the pulse wave amplitude which have been detected prior to the systolic blood pressure and which have been stored in the memory are deleted.

Therefore, the capacity of the memory will be effectively used by storing only such data regarding the cuff pressure and the pulse wave amplitude which are necessary to determine the blood pressure.

Further, in accordance with the present invention, when the diastolic blood pressure which is determined by the first peak on the curve of the varying pulse wave amplitude, is judged not to be erroneous, the subsequent operation will be halted. Also, even if there is the second peak on the curve of the varying pulse wave amplitude which is lower than the first peak, the provisionally determined systolic blood pressure and diastolic blood pressure on the basis of the first peak on the curve of the varying pulse wave amplitude are concluded as the final blood pressure.

Accordingly, when the blood pressure can be precisely determined on the basis of the first peak on the curve of the varying pulse wave amplitude, the subsequent operation will be halted, thereby rapidly completing the blood pressure measurement.

DETAILED DESCRIPTION OF THE PREFERRED EMBODIMENT

A preferred embodiment of the present invention will now be described with reference to the drawings. It is not intended that the present invention is limited to the described embodiment.

Figure 1:
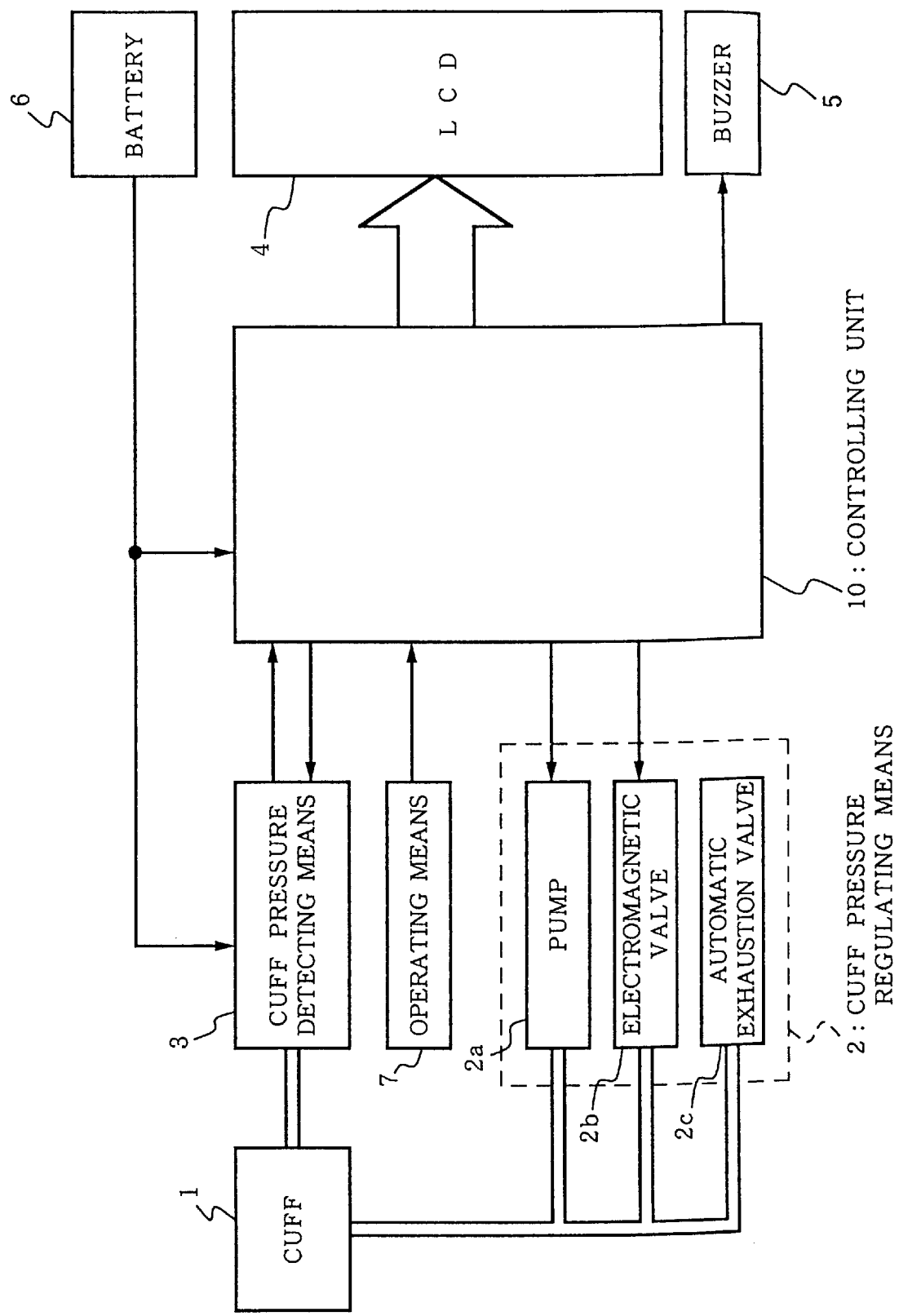
FIG. 1 is a block diagram illustrating an embodiment of the oscillometric type electronic sphygmomanometer of the present invention.

In FIG. 1, a schematic arrangement of the an oscillometric type electronic sphygmomanometer according to this embodiment of the present invention.

The electronic sphygmomanometer of FIG. 1 comprises cuff 1 for compressing an artery of a testee, cuff pressure regulating means 2 for increasing or decreasing the pressure in cuff 1 up to or down to a predetermined pressure, respectively, cuff pressure detecting means 3 for detecting the pressure in cuff 1 and outputting the analog-to-digital-converted result of the detection, and control unit 10 for measuring the blood pressure of the testee on the basis of a signal from cuff pressure detecting means 3 and for forwarding a control signal to cuff pressure regulating means 2 and cuff pressure detecting means 3.

This electronic sphygmomanometer further comprises liquid crystal display 4 for displaying measured values, buzzer 5 for notifying the completion of the blood pressure measurement, battery 6 for supplying power to the sphygmomanometer, and operational means 7 for operating these elements.

Cuff pressure regulating means 2 is configured to include pump 2a, electromagnetic valve 2b, and automatic exhaustion valve 2c. This cuff pressure regulating means 2 is driven to function once measurement is initiated by operational means 7 after cuff 1 is wrapped around the testee's brachium and the like.

When a drive signal is forwarded to cuff pressure regulating means 2 via controlling unit 10, cuff pressure regulating means 2 begins to provide pressure to cuff 1 by supplying air thereto. When the cuff pressure increases and reaches a predetermined value, 200 mmHg, for example, automatic exhaustion valve 2c functions to decrease the cuff pressure by gradually exhausting the pressure within cuff 1 at, for example, the rate of 5 mmHg/sec. When cuff pressure regulating means 2 receives from controlling unit 10 a signal indicative of the completion of the blood pressure measurement, cuff pressure regulating means 2 will have electromagnetic valve operated so as for the pressure within cuff 1 to be liberated and returned to the atmospheric pressure.

Controlling unit 10 will now be described. Controlling unit 10 receives, as an input, a signal from cuff pressure detecting means 3 and operative means 7 and controls the operations of the elements constituting the oscillometric type electronic sphygmomanometer, which are cuff pressure regulating means 2, cuff pressure detecting means 3, liquid crystal display 4, and buzzer 5, so that the blood pressure value will be determined.

Figure 2:
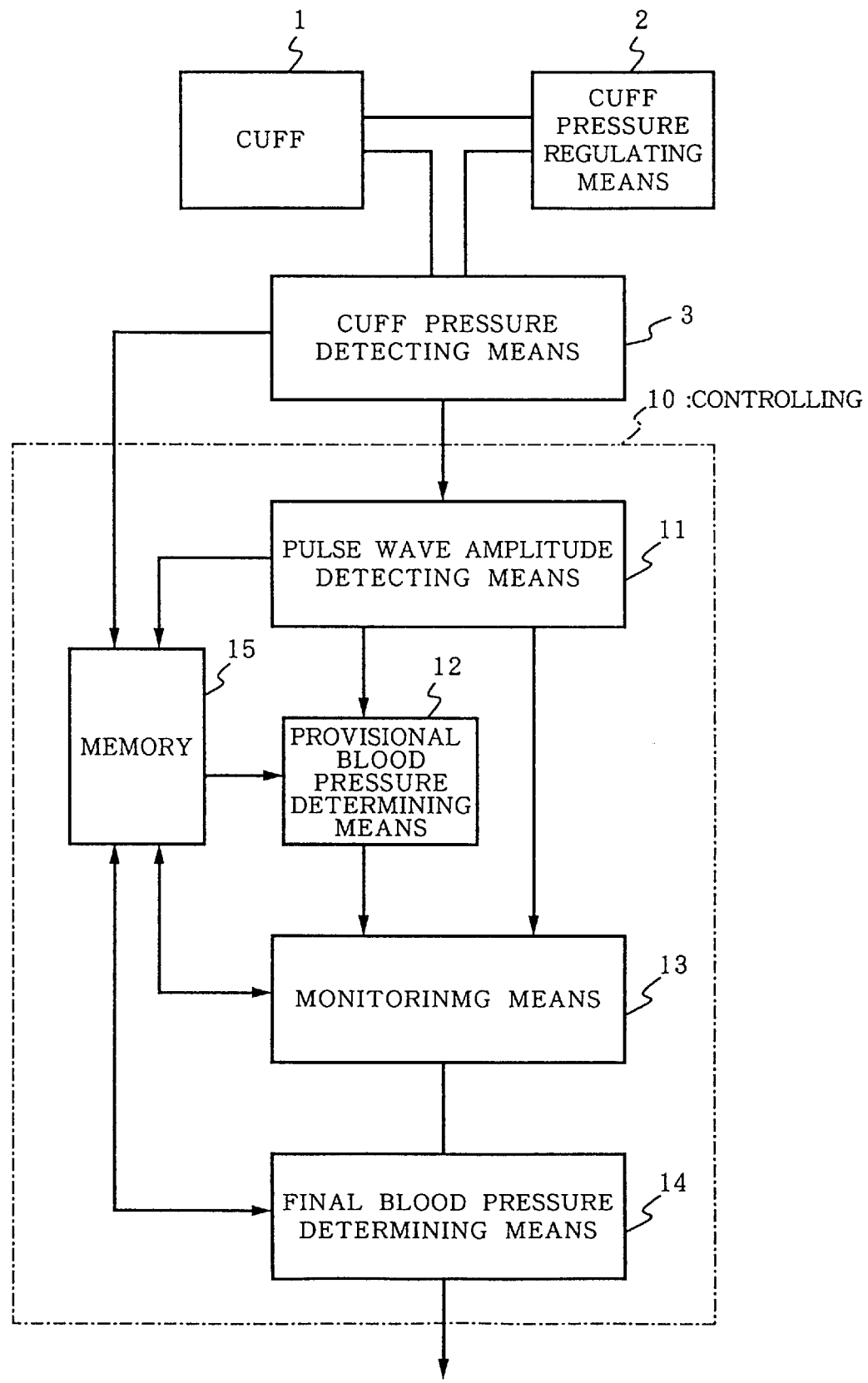
FIG. 2 is a more detailed block diagram of a portion of the control unit of FIG. 1.

FIG. 2 is a block diagram illustrating an exemplary embodiment of the blood pressure determination system in controlling unit 10.

The blood pressure determination system comprises pulse wave amplitude detecting means 11, means for determining the provisional blood pressure 12, monitoring means 13, means for determining the final blood pressure 14, memory 15, and controlling means for controlling these means (not shown in the figure).

Pulse wave amplitude detecting means 11 detects the magnitude of the pulse wave amplitude corresponding to the cuff pressure which decreases (for example, by 5 mmHg from 200 mmHg) on the basis of the signal from cuff pressure detecting means 3. The data representative of the relationship between these cuff pressure and the pulse wave amplitude will be stored in memory 15.

The provisional blood pressure determining means 12 receives, as an input, the pulse wave amplitude signal from cuff pressure detecting means 3 and determines, when the pulse wave amplitude signal varies itself as forming a peak, the cuff pressure when the pulse wave amplitude is at its maximum value is provisionally determined as the mean the blood pressure, the cuff pressure corresponding to the pulse wave amplitude of the high pressure side which is equivalent to 50% of the maximum pulse wave amplitude as the systolic blood pressure, the cuff pressure corresponding to the pulse wave amplitude of the low pressure side which is equivalent to 70% of the maximum pulse wave amplitude as the diastolic blood pressure. These data will be stored in memory 15.

This the blood pressure determination system will continue, after the blood pressure is provisionally determined, to detect the pulse wave amplitude and to output the result thereof until the cuff pressure decreases below the diastolic blood pressure value by a predetermined pressure (for example, −50 mmHg to −10 mmHg).

If the diastolic blood pressure provisionally determined by the provisional blood pressure determining means 12 is higher than a preset value, monitoring means 13 monitors the pulse wave amplitude outputted from the pulse wave amplitude detecting means 11 while the cuff pressure is lowered from this provisionally determined diastolic blood pressure by a predetermined value down to a pressure (monitored pressure). If a pulse wave amplitude is detected which is higher than the provisionally determined systolic blood pressure above while the cuff pressure is lowered down to the monitored pressure, monitoring means 13 determines that a second peak has appeared on the curve of the varying pulse wave amplitude.

The blood pressure determination system thus continues to further detect the pulse wave amplitude even after the cuff pressure has been lowered from the provisionally determined diastolic blood pressure by a predetermined pressure value.

On the other hand, if the monitoring means 13 does not detect a pulse wave amplitude which is higher than the provisionally determined diastolic blood pressure above while the cuff pressure is lowered by a predetermined pressure value, it will be determined that a second peak has not appeared on the curve of the varying pulse wave amplitude.

The final blood pressure determining means 14 determines, when a second peak has appeared on the curve of the varying pulse wave amplitude, the mean the blood pressure, the systolic blood pressure, and the diastolic blood pressure on the basis of the cuff pressure corresponding to the pulse wave amplitude at its maximum value which forms the second peak, the cuff pressure which is 70% of the maximum value, and the cuff pressure which is 50% of the maximum value.

On the other hand, the final blood pressure determining means 14 determines, when it has been determined that a second peak has not appeared, the mean the blood pressure, the systolic blood pressure, and the diastolic blood pressure determined by the provisional blood pressure determining means 12 will be determined as the final blood pressure. In such a case, the subsequent measurement will be halted and the resulted measurement values will be displayed, thereby accelerating the blood pressure measurements.

Figure 3:
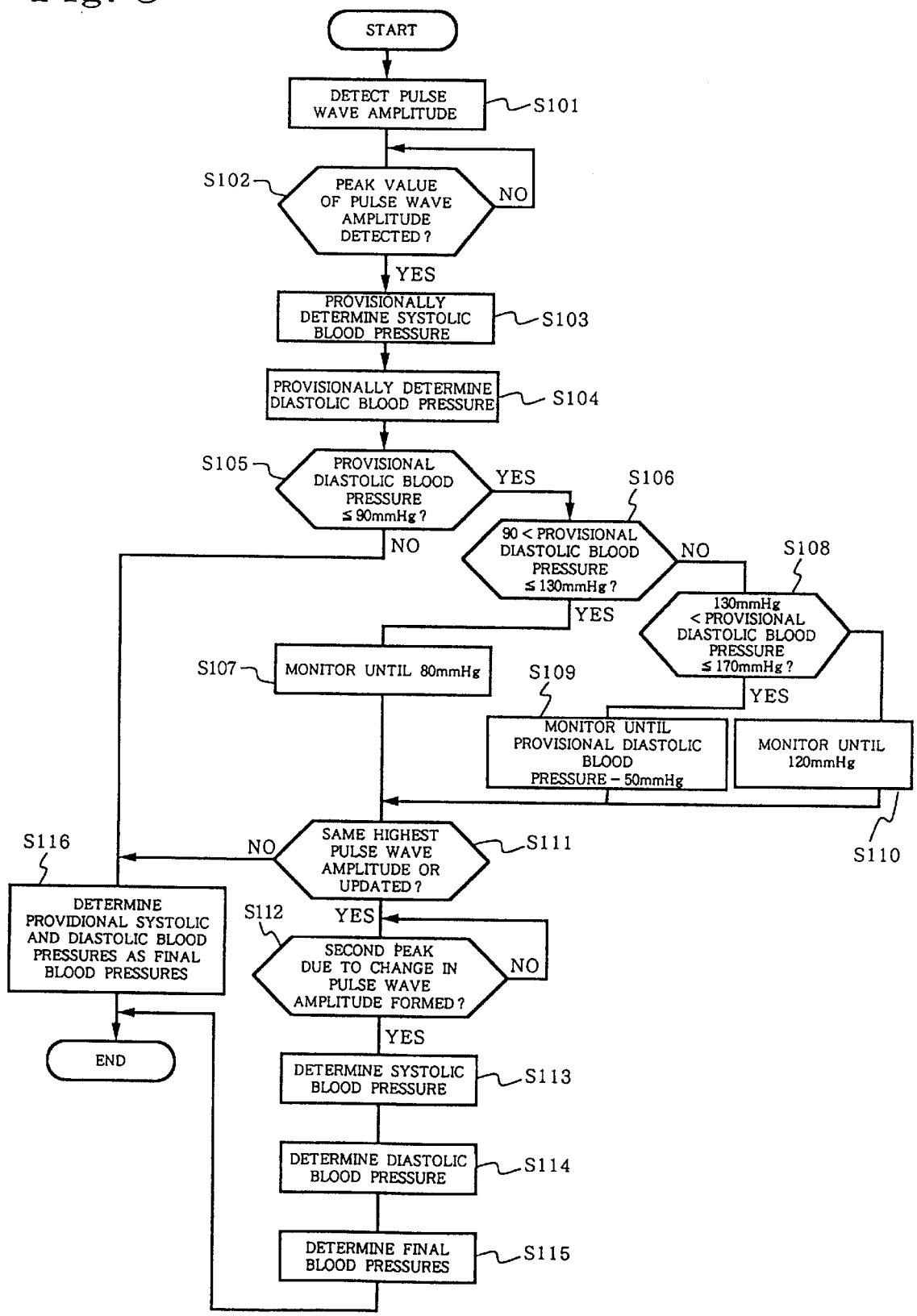
FIG. 3 is a flow diagram describing the operation of an oscillometric type electronic sphygmomanometer according to one embodiment of the present invention.
Figure 4:
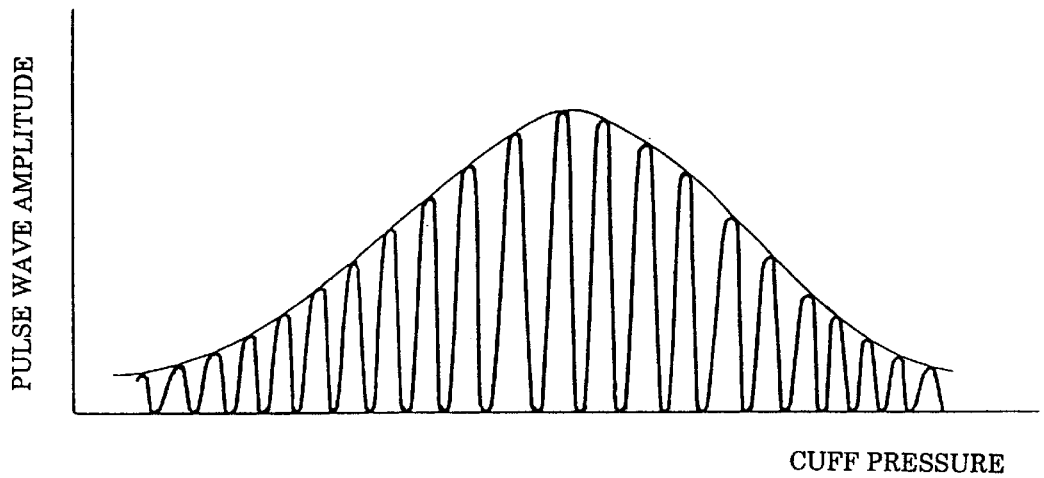
FIG. 4 is a graph illustrating an exemplary curve formed by the varying pulse wave amplitude containing a single peak.

An exemplary operation of the oscillometric type electronic sphygmomanometer in accordance with the present invention will now be described in referring to the flow chart of FIG. 3.

Figure 5:
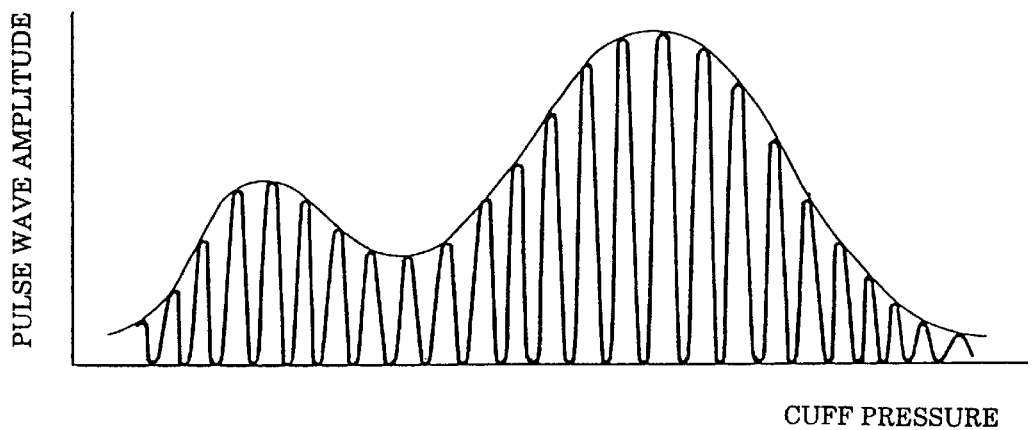
FIG. 5 is a graph illustrating an exemplary curve formed by the varying pulse wave amplitude containing two peaks.

The following description will be done assuming that the curve of the varying pulse wave amplitude of FIG. 5 has been obtained.

After cuff 1 is first wrapped as a compression band around the brachium and the like of the testee or patient, the operational means is activated to start compression by having air supplied by pump 2a of the said cuff pressure regulating means 2, to increase the pressure in cuff 1 up to, for example, 200 mmHg by operating a compression setting switch, then to gradually decrease the cuff pressure at the rate of approximately 5 mmHg/sec by using automatic exhaustion valve 2c, and initiate the measurement.

Figure 6:
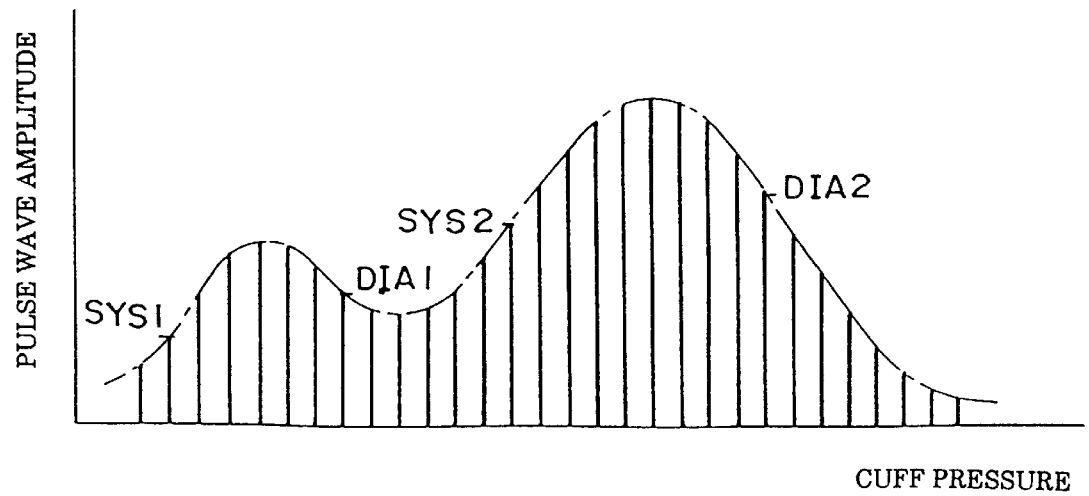
FIG. 6 is a graph illustrating another exemplary curve formed by the varying pulse wave amplitude containing two peaks.

Pulse wave amplitude detecting means 11 performs the pulse wave amplitude detection (S101) on the basis of the pulse wave data as shown in FIG. 6, which has been obtained from the cuff pressure detecting means by an analog-digital conversion.

When the maximum value of the pulse wave amplitude, which is a peak value where the increasing pulse wave amplitude begins to decrease (the first peak on the curve of the varying pulse wave amplitude), is detected, the provisional blood pressure determining means 12 determines (S103, S104) provisionally the systolic blood pressure value which is provisionally determined as being the systolic blood pressure(SYS1) and provisionally the diastolic blood pressure value (DIA1) using the oscillometric method as shown in FIG. 6.

Once the provisionally systolic and diastolic blood pressure values are determined, monitoring means 13 determines if the provisional systolic blood pressure value is higher than a preset value. If so, the pulse wave amplitude will continue to be detected until the cuff pressure decreases by a predetermined value, so that the change in the pulse wave amplitude may be monitored.

An example will now be given. When the provisional diastolic blood pressure value is lower than a preset vale of 90 mmHg, it will be regarded as being normal. When it is higher than the preset vale of 90 mmHg, however, the pulse wave amplitude will continue to be detected (S105). When the provisional diastolic blood pressure value is between 90 mmHg and 130 mmHg, the pulse wave amplitude will continue to be detected until the cuff pressure decreases to 80 mmHg (S106, S107). When the provisional diastolic blood pressure value is in the range from 130 mmHg to 170 mmHg, the pulse wave amplitude will continue to be detected until the cuff pressure which is uniformly 50 mmHg lower than the provisional diastolic blood pressure value (S108, S109). When the provisionally the diastolic blood pressure value is more than 170 mmHg, the pulse wave amplitude will continue to be detected until the cuff pressure decreases to reach 120 mmHg (S110).

The particular numerical values above have been determined owing to the clinical experiences. That is, it has been clinically known that, although the first peak is formed for some reason on the curve of the varying pulse wave amplitude and a the diastolic blood pressure is erroneously measured, a true varying waveform will be formed (i.e., the peak value of the second peak on the curve of the varying pulse wave amplitude will be detected) if the pulse wave amplitude continues to be detected until the cuff pressure decreases approximately 50 mmHg below the erroneously determined diastolic blood pressure.

It should be understood by those skilled in the art that the particular values above may be conveniently changed depending upon the conditions under which the blood pressure is being measured.

If a previously detected maximum value of the pulse wave amplitude is replaced (S111) by a newly detected maximum value while the pulse wave amplitude continues to be detected and monitored, the pulse wave amplitude further continues to be detected (S112) until a maximum value of the pulse wave amplitude is detected again and the second peak is formed on the curve of the pulse wave amplitude.

Then, the systolic (SYS2) and the diastolic (DIA2) blood pressure values will be determined (S113, S114) using the oscillometric method as shown in FIG. 6 and these values will be displayed on the liquid crystal display 4 of FIG. 1 after being determined as the final blood pressure (S115).

When the diastolic blood pressure determined on the basis of the second peak on the curve of the varying pulse wave amplitude is still high, the steps of S111–S115 may be repeated.

When the diastolic blood pressure provisionally determined at step S105 is equal to or lower than 90 mmHg and when the maximum pulse wave amplitude has not been updated while the cuff pressure decreases by a predetermined value, the provisionally determined the systolic and the diastolic blood pressure will be determined as the final blood pressure (S116) and displayed on the liquid crystal display 4 of FIG. 1.

When the measurement of the blood pressure is thus terminated, electromagnetic valve 2b will be opened by a signal from controlling unit 10, which will rapidly exhaust the air within the cuff.

Figure 7:
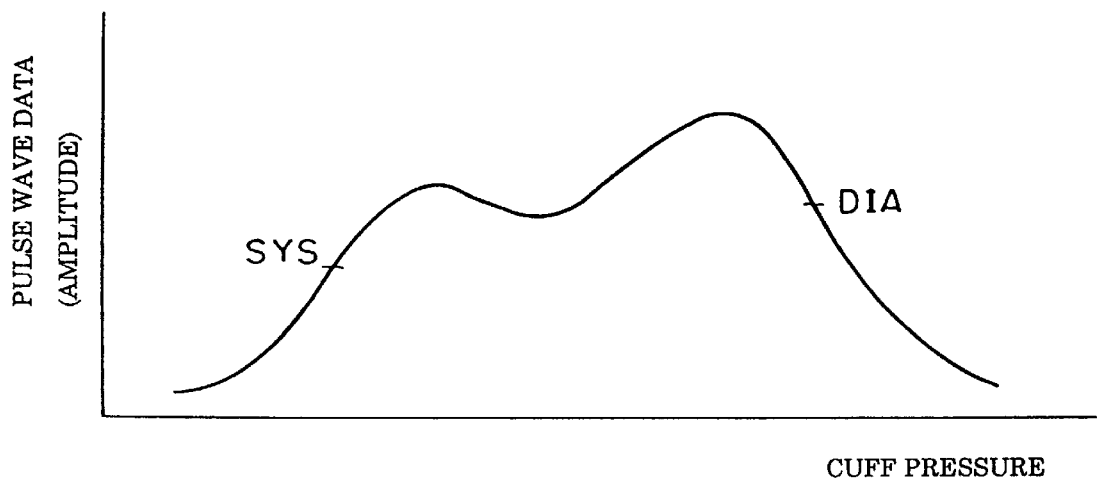
FIG. 7 is a graph illustrating another exemplary curve formed by the varying pulse wave amplitude containing two peaks.

When the two peaks have not been formed in such manner as illustrated in FIG. 7, by which a the diastolic blood pressure can not be obtained from the first peak on the curve of the varying pulse wave amplitude, the blood determination system of the present invention will regard the waveform as illustrated in FIG. 7 as being a waveform having one peak, from which the systolic (SYS) and the diastolic (DIA) blood pressure will be determined.

When the pulse wave amplitude detected while being monitored decreases from the pulse wave amplitude corresponding to the provisionally determined systolic blood pressure and then forms the said second peak on the curve of the varying pulse wave amplitude, the systolic and the diastolic blood pressure determined on the basis of the curve forming the said second peak will be determined as the final blood pressure.

Also, when the pulse wave amplitude detected while being monitored forms the said second peak on the curve of the varying pulse wave amplitude without decreasing from the pulse wave amplitude corresponding to the provisionally determined systolic blood pressure, the provisionally determined systolic blood pressure will be determined as the final systolic blood pressure and the diastolic blood pressure determined on the basis of the curve forming the said second peak will be determined as the final diastolic blood pressure.

It will be possible to measure the blood pressure precisely, regardless of the shape of the curve which contains one or more peaks.

Figure 8:
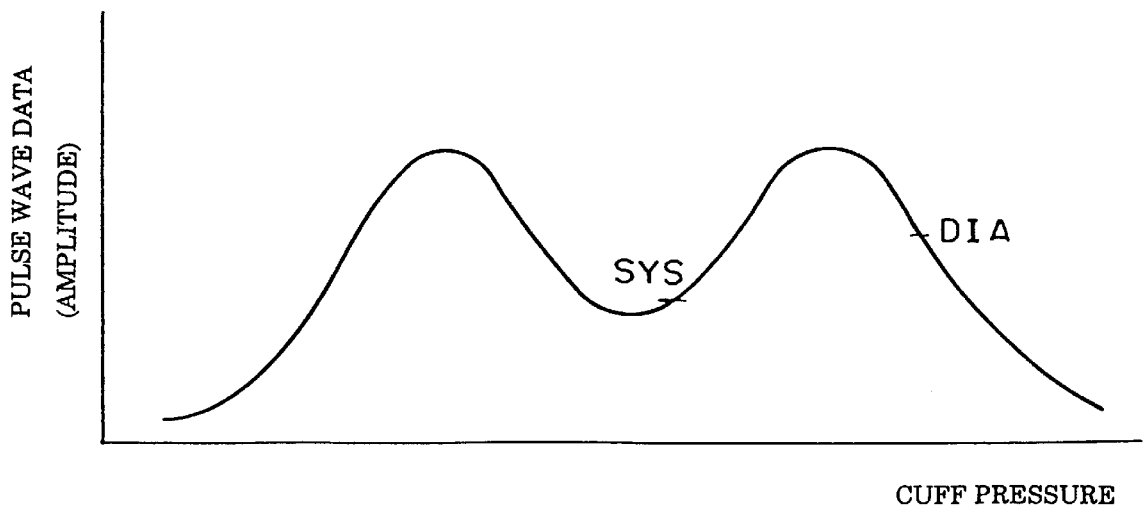
FIG. 8 is a graph illustrating another exemplary curve formed by the varying pulse wave amplitude containing two peaks.

Further, when the two peaks have been formed on the curve of the varying pulse wave amplitude in such manner as illustrated in FIG. 8, wherein the maximum pulse wave amplitude values for the first and the second peaks are the same, the systolic (SYS) and the diastolic (DIA) the blood pressure will be determined on the basis of the curve which forms the second peak.

This principle has been empirically employed since the clinical experiences show that the second peak provides us with a better result.

By employing an oscillometric type electronic sphygmomanometer in accordance with the present invention, a precise measurement can be obtained even if more than two peaks are formed on the curve of the varying pulse wave amplitude because of disordered breathing or physical movement of the testee.

It will now be described how memory 15 will be used. Memory 15, which normally stores the data associating the cuff pressure with the pulse wave amplitude, is normally capable of storing 37 data. Accordingly, when the number of data increases, there will be a memory shortage, which result in a measurement error of the blood determination system.

In order to avoid such a situation, in this oscillometric type electronic sphygmomanometer in accordance with an embodiment of the present invention, data of no value for use will not be stored in memory 15 and/or data of no future value for use will be deleted from memory 15.

For example, while a curve of the varying pulse wave amplitude on which two peaks are formed is being monitored, the pulse wave amplitude which is below the 50% level of the maximum pulse wave amplitude forming the first peak contributes nothing to the determination of the blood pressure. Accordingly, such useless data will not be stored in memory 15.

On the other hand, after the systolic and the diastolic blood pressure are determined on the basis of the curve of the varying pulse wave amplitude on which the first peak is formed, if the maximum pulse wave amplitude value forming the second peak is equal to or higher than the maximum pulse wave amplitude value forming the first peak, which assures that a new set of the systolic and the diastolic blood pressure will be determined, the data stored in memory 15 which are necessary for determining the previous the systolic and the diastolic blood pressure will be deleted.

Other data which are or have become unnecessary for determining the blood pressure will not be stored in memory 15 but will be deleted from memory 15.

Thus a memory with a limited storing capacity may be used for the present invention, thereby lowering the cost.

What is claimed is:

1. An oscillometric type electronic sphygmomanometer, comprising:
   a cuff,
   cuff pressure detecting means connected to the cuff to detect a cuff pressure, and
   control means receiving a signal from the cuff pressure detecting means to obtain a varying pulse wave amplitude and determining systolic and diastolic blood pressures on a basis of a peak formed by variance in the pulse wave amplitude, wherein said control means determines at least the diastolic blood pressure on a basis of the cuff pressure and pulse wave amplitude forming a peak which has a maximum pulse wave amplitude value when more than two peaks are formed on a curve of the varying pulse wave amplitude.

2. The oscillometric type electronic sphygmomanometer according to claim 1, wherein said control means includes:
   pulse wave detecting means for detecting the varying pulse wave amplitude on a basis of a signal from the cuff pressure detecting means,
   provisional blood pressure determining means for determining provisional systolic and diastolic blood pressures on a basis of the curve of the varying pulse wave amplitude which forms a first peak,
   monitoring means for continuously monitoring the varying pulse wave amplitude until the cuff pressure decreases below the provisionally determined diastolic blood pressure by a predetermined pressure when the provisionally determined diastolic blood pressure is higher than a preset value, and
   final blood pressure determining means for continuously detecting a new maximum pulse wave amplitude when the pulse wave amplitude detected while being monitored is equal to or higher than the maximum pulse wave amplitude value, said final blood pressure determining means determining at least the diastolic blood pressure on a basis of the curve of the varying pulse wave amplitude, which has the maximum pulse wave amplitude value and forms a second peak.

3. The oscillometric type electronic sphygmomanometer according to claim 2, wherein said control means operates such that when the pulse wave amplitude detected while being monitored decreases from the pulse wave amplitude corresponding to the provisionally determined systolic blood pressure and then forms the second peak on the curve of the varying pulse wave amplitude, the systolic and diastolic blood pressures determined on a basis of the curve forming the second peak are determined as final blood pressures.

4. The oscillometric type electronic sphygmomanometer according to claim 3, wherein said control means includes a memory and operates such that if the pulse wave amplitude and the cuff pressure are detected and stored in the memory and then a blood pressure is determined on a basis of a relationship between the pulse wave amplitude and the cuff pressure, data representative of the pulse wave amplitude and the cuff pressure are stored in the memory only when the pulse wave amplitude detected while being monitored is higher than a predetermined ratio of the maximum pulse wave amplitude on the curve of the varying pulse wave amplitude which forms the first peak.

5. The oscillometric type electronic sphygmomanometer according to claim 3, wherein said control means operates such that when the systolic and diastolic blood pressures are determined on a basis of the curve of the varying pulse wave amplitude which forms the second peak, data representative of the cuff pressure and the pulse wave amplitude which have been detected prior to the systolic blood pressure and which have been stored in a memory are deleted.

6. The oscillometric type electronic sphygmomanometer according to claim 2, wherein said control means operates such that when the pulse wave amplitude detected while being monitored forms the second peak on the curve of the varying pulse wave amplitude without decreasing from the pulse wave amplitude corresponding to the provisionally determined systolic blood pressure, the provisionally determined systolic blood pressure is determined as a final systolic blood pressure and a diastolic blood pressure determined on a basis of the curve forming the second peak is determined as a final diastolic blood pressure.

7. The oscillometric type electronic sphygmomanometer according to claim 4, wherein said control means includes a memory and operates such that if the pulse wave amplitude and the cuff pressure are detected and stored in the memory and then a blood pressure is determined on a basis of a relationship between the pulse wave amplitude and the cuff pressure, data representative of the pulse wave amplitude and the cuff pressure are stored in the memory only when the pulse wave amplitude detected while being monitored is higher than a predetermined ratio of the maximum pulse wave amplitude on the curve of the varying pulse wave amplitude which forms the first peak.

8. The oscillometric type electronic sphygmomanometer according to claim 6, wherein said control means operates such that when the systolic and diastolic blood pressures are determined on a basis of the curve of the varying pulse wave amplitude which forms the second peak, data representative of the cuff pressure and the pulse wave amplitude which have been detected prior to the systolic blood pressure and which have been stored in a memory are deleted.

9. The oscillometric type electronic sphygmomanometer according to claim 2, wherein said control means includes a memory and operates such that if the pulse wave amplitude and the cuff pressure are detected and stored in the memory and then a blood pressure is determined on a basis of a relationship between the pulse wave amplitude and the cuff pressure, data representative of the pulse wave amplitude and the cuff pressure are stored in the memory only when the pulse wave amplitude detected while being monitored is higher than a predetermined ratio of the maximum pulse wave amplitude on the curve of the varying pulse wave amplitude which forms the first peak.

10. The oscillometric type electronic sphygmomanometer according to claim 9, wherein said control means operates such that when the systolic and diastolic blood pressures are determined on a basis of the curve of the varying pulse wave amplitude which forms the second peak, data representative of the cuff pressure and the pulse wave amplitude which have been detected prior to the systolic blood pressure and which have been stored in a memory are deleted.

11. The oscillometric type electronic sphygmomanometer according to claim 1, wherein said control means determines provisional systolic and diastolic blood pressures on a basis of the curve of the varying pulse wave amplitude which forms a first peak, when the provisionally determined diastolic blood pressure is below a preset value, said provisionally determined systolic and diastolic blood pressures being determined as final blood pressures.

12. The oscillometric type electronic sphygmomanometer according to claim 1 wherein said control means includes:
  pulse wave detecting means for detecting the varying pulse wave amplitude on a basis of a signal from the cuff pressure detecting means,
  provisional blood pressure determining means for determining provisional systolic and diastolic blood pressures on a basis of the curve of the varying pulse wave amplitude which forms a first peak,
  monitoring means for continuously monitoring the varying pulse wave amplitude until the cuff pressure decreases below the provisionally determined diastolic blood pressure by a predetermined pressure when the provisionally determined diastolic blood pressure is higher than a preset value, and
  final blood pressure determining means for determining that the provisionally determined systolic and diastolic blood pressures are determined as the final blood pressures when the pulse wave amplitude detected while being monitored has not updated a maximum pulse wave amplitude value.

13. An oscillometric type electronic sphygmomanometer comprising a cuff, cuff pressure detecting means, cuff pressure regulating means, and controlling means for determining the systolic and the diastolic blood pressure by using the oscillometric method, wherein the controlling means includes:
  pulse wave detecting means for detecting a pulse wave amplitude on the basis of a signal from the cuff pressure detecting means;
  the provisional blood pressure determining means for provisionally determining at least a the diastolic blood pressure on the basis of a maximum pulse wave amplitude from the pulse wave detecting means;
  monitoring means for detecting and monitoring the pulse wave amplitude when the provisionally determined diastolic blood pressure is higher than a preset value; and the final blood pressure determining means for determining, when a pulse wave amplitude detected while being monitored is equal to or higher than the maximum pulse wave amplitude, the systolic blood pressure on the basis of the newly detected maximum pulse wave amplitude value.

* * * * *